(12) United States Patent
Lin et al.

(10) Patent No.: US 11,124,761 B2
(45) Date of Patent: Sep. 21, 2021

(54) STABILIZATION OF ENZYME-IMMOBILIZED HYDROGELS FOR EXTENDED HYPOXIC CELL CULTURE

(71) Applicant: Indiana University Research and Technology Corporation, Indianapolis, IN (US)

(72) Inventors: Chien-Chi Lin, Indianapolis, IN (US); Camron Scott Dawes, Urbana, IN (US); Heiko Konig, Carmel, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 87 days.

(21) Appl. No.: 16/212,212

(22) Filed: Dec. 6, 2018

(65) Prior Publication Data

US 2019/0177683 A1 Jun. 13, 2019

Related U.S. Application Data

(60) Provisional application No. 62/595,735, filed on Dec. 7, 2017.

(51) Int. Cl.
| | | |
|---|---|---|
| C12N 5/00 | (2006.01) | |
| G01N 33/50 | (2006.01) | |
| C12M 1/12 | (2006.01) | |
| C12M 1/00 | (2006.01) | |

(52) U.S. Cl.
CPC ............ *C12N 5/0018* (2013.01); *C12M 23/20* (2013.01); *C12M 25/00* (2013.01); *C12M 25/14* (2013.01); *C12N 5/0062* (2013.01); *C12Y 101/03004* (2013.01); *G01N 33/5091* (2013.01); *C12N 2500/02* (2013.01); *C12N 2500/34* (2013.01); *C12N 2500/50* (2013.01); *C12N 2500/60* (2013.01); *C12N 2501/70* (2013.01)

(58) Field of Classification Search
None
See application file for complete search history.

(56) References Cited

PUBLICATIONS

Tehrani, Sepehr Mastour; et al; "PEGMA-Based Microgels: A Thermoresponsive Support for Enzyme Reactions" Macromolecules, 49, 8711-8721,2016 (Year: 2016).*

Paz-Alfaro, Karina; et al; "Trehalose-mediated thermal stabilization of glucose oxidase fromAspergillus niger" Journal of Biotechnology, 141, 130-136, 2009 (Year: 2009).*

O'Shea, Timothy; et al; "Covalent Incorporation of Trehalose within Hydrogels for Enhanced Long-Term Functional Stability and Controlled Release of Biomacromolecules" Advanced Healthcare Materials, 4, 1802-1812, 2015 (Year: 2015).*

Camron S. Dawes, Heiko Konig, Chien-Chi Lin, "Enzyme-immobilized hydrogels to create hypoxia for in vitro cancer cell culture", 2017; 34 pages.

* cited by examiner

*Primary Examiner* — David W Berke-Schlessel
(74) *Attorney, Agent, or Firm* — Faegre Drinker Biddle & Reath LLP

(57) ABSTRACT

Embodiments of the current invention include a hydrogel formed from crosslinked polyethylene glycol into which acrylated glucose oxidase has been immobilized through crosslinking to the gel. These hydrogels can be used to create hypoxia under ambient conditions for at least 72 hours and can be used to create hypoxic gradients. These embodiments permit the study of cells under a variety of hypoxic conditions.

10 Claims, 14 Drawing Sheets

STABILIZATION OF ENZYME-IMMOBILIZED HYDROGELS FOR EXTENDED HYPOXIC CELL CULTURE

CROSS REFERENCE TO RELATED APPLICATION

This application claims the benefit of U.S. Provisional Application No. 62/595,735, filed Dec. 7, 2017, entitled STABILIZATION OF ENZYME-IMMOBILIZED HYDROGELS FOR EXTENDED HYPOXIC CELL CULTURE, the disclosure of which is incorporated herein by reference in its entirety.

STATEMENT OF GOVERNMENTAL RIGHTS

This invention was made with government support under grant 1452390 awarded by the National Science Foundation. The Government has certain rights in the invention.

FIELD OF THE INVENTION

This invention relates generally to the design and characterization of enzyme-immobilized hydrogels suitable for long term storage, and capable of creating solution hypoxia under ambient conditions.

BACKGROUND AND SUMMARY

Hypoxia, the lack of adequate oxygen ($O_2$) supply in cells and tissues, is a physiological condition of many healthy and diseased tissues in the body. For example, $O_2$ concentration is around twenty percent in the lungs; near thirteen percent in the alveoli; roughly five percent in the circulatory system and the bone marrow; and below five percent in multicellular tissues. Hypoxia is implicated in both normal physiological events and pathological conditions, including ischemia, tumors, and inflamed tissues. As such, $O_2$ concentration should be considered as a critical experimental condition when performing in vitro cell studies.

Hypoxia stabilizes the expression of hypoxia inducible factors (HIFs), which are heterodimeric transcription factors that regulate many downstream genes and cell fate processes including proliferation, metabolism, apoptosis, stress response, angiogenesis, and migration. Hypoxia is also a key factor in regulating the growth of tumors and cancer cell drug resistance.

The gold standard to induce hypoxia ($[O_2]<5\%$) for in vitro cell culture is through use of a cell culture chamber with controlled gas supplies (i.e., a hypoxic chamber). However, the time needed to reach equilibrium of $O_2$ partial pressure between the chamber atmosphere and the culture medium could take several hours. Another challenge of using a hypoxic chamber is that $O_2$ diffusion from the air to the cell culture media occurs rapidly once the culture plates are removed from the hypoxic chamber. Studies have shown that even brief exposure of some cells to ambient air would cause drastic changes in the expression of certain hypoxia-related genes. For this reason, a glovebox is required to maintain hypoxia throughout an experiment. The high front-end cost and dedicated space required for a hypoxic chamber system also limits its implementation to selected laboratories. In addition, it is challenging to perform real-time imaging or other instrument-based live cell assays under hypoxic conditions, even with the use of a glovebox. Furthermore, one hypoxic chamber system can provide only one fixed $O_2$ tension for one experiment, which significantly hinders the progress of scientific discovery related to varied $O_2$ tensions (e.g., hypoxia gradient, multiplex hypoxic drug testing, etc.).

Another method to induce hypoxia for cell culture is the introduction of pre-equilibrated media with lower $O_2$ tension into the cell culture vessels, such as bioreactors or microfluidic devices. Bioreactors are the standard for scale-up production of cells or biological products, but are not ideal for mechanistic studies of hypoxia-induced cellular response. On the other hand, a microfluidic culture system permits real-time imaging of hypoxic cell culture and allows creation of complex hypoxia patterns within the confined microenvironment. For example, chemical scavengers have been used to reduce aqueous $O_2$ content within a patterned array of cells in the wells of a microfluidic device with geometry matching that of a 96-well plate. This method is beneficial in that multiple $O_2$ profiles can be developed rapidly through pre-equilibrated media in different wells of a single device. However, setting up microfluidic cell culture requires special instruments and project-specific microfluidic design. The applicability of such a system in higher or enhanced-throughput analysis (e.g., drug screening and testing under various hypoxic conditions) is limited, nor is it an easy task to integrate microfluidic system with three-dimensional (3D) cell culture.

Hypoxic response in the cells can also be simulated using chemicals that upregulate or stabilize the expression of HIF1α. Cobalt chloride ($CoCl_2$) or desferrioxamine are two examples of such chemicals. Although this is a relatively simple strategy to mimic hypoxic response in the cells, the use of chemical means only regulates cellular and molecular responses directly downstream of HIF. Furthermore, these chemicals could affect cell survival, metabolism, and morphology differently in comparison to real $O_2$ deprivation.

Recently, $O_2$-consuming enzymatic reactions have been developed as an alternative to the aforementioned methods. The most notable example is the use of glucose oxidase (GOX) and catalase (CAT). GOX oxidizes β-D-glucose while consuming $O_2$ to produce gluconolactone and hydrogen peroxide ($H_2O_2$). CAT is commonly added to reduce the cytotoxic $H_2O_2$ to one mole of water and a half mole of $O_2$. This system has been used to induce hypoxia in solutions and microfluidic devices. The use of GOX/CAT is beneficial, in that the system provides a rapid onset of hypoxia, usually within a few minutes. One drawback to any GOX system however, is the production of hydrogen peroxide, a reactive oxygen species (ROS) whose accumulation would not only cause undesired cellular response, but also inactivate both GOX and CAT. Thus far, the applications of GOX/CAT system have been focused on glucose sensing and pH-induced responses, though $O_2$ concentrations were monitored. Some recent work has started to explore the ability of GOX/CAT reactions to induce hypoxia for in vitro cell culture. The GOX/CAT system has also been adapted to 3D printed inserts, where GOX and CAT were coated on printed disks. The degrees of solution hypoxia were controlled by the distance between the enzyme-immobilized disks and the solution in the culture plate. In that design, hypoxia conditions (between zero and about twelve percent $O_2$) were maintained for up to five hours, and the system was used to induce hypoxic response in peritoneal macrophages.

Other enzymes (e.g., laccase) have also been used to create hypoxia. In the laccase system, a fixed amount of substrate (i.e., ferulic acid, FA) is immobilized to a polymer backbone. The FA-immobilized polymer is then crosslinked by a laccase-mediated enzymatic reaction, which also consumes $O_2$.

Some aspects of the invention provide materials and methods that can be used to create and/or maintain hypoxic conditions in hydrogels under ambient conditions without the need for specialized, expensive equipment.

Some aspects of the invention include creating a hypoxic gradient using a hydrogel.

Still other aspects of the invention include materials and/or methods for creating hydrogel compositions that are stable for long-term storage.

Still other aspects of the invention include using the inventive compositions and/or methods to culture cells which may grow better under low concentrations of oxygen. In some embodiments these cells are cancer cells.

The invention described herein includes a composition, comprising a hydrogel formed from crosslinked polyethylene glycol into which PEG-ylated glucose oxidase has been immobilized through crosslinking to the gel. D-trehalose can be added into the hydrogel composition so as to stabilize the enzyme against changes in temperature. Said gel can be prepared for long term storage by lyophilisation immediately after gelation, and stored at about −20° C. The GOX-immobilized hydrogel can be used with in a buffer containing glutathione. The GOX-immobilized hydrogel can also be used in devices for creating hypoxia gradients by placing one of said hydrogels at one end of a channel slide, or by placing two of said hydrogels at both ends of a channel slide. These compositions and devices can be used to study cells, including stem cells, adult cells, and cancer cells, under hypoxic conditions without the need for a glove box or other specialized equipment.

The GOX-immobilized hydrogel can establish and sustain in vitro hypoxic conditions (less than 5 percent oxygen) for 6 to 24 hours while under ambient air conditions (with constant oxygen diffusion from the air-liquid interface). The activity of the enzymes within the hydrogels can be preserved past 24 hours through the addition of trehalose. The duration of solution hypoxia can be extended to 72 hours through the addition of glutathione to the solution.

An embodiment wherein the embodiment is a composition comprising a hydrogel formed from at least one polymer building block selected from the group consisting of: polyethylene glycol; (polyethylene-glycol)-diacrylate; polyvinyl alcohol; polyglycerol; collagen; gelatin; chitosan; heparin; fibrinogen; hyaluronic acid; chondroitin sulfate; pullulan; xylan; dextran; alginate; silk fibroin; or derivatives of these polymers; at least a portion of at least one enzyme selected from the group consisting of: acrylated glucose oxidase; acrylated bilirubin oxidase tyrosinase; acrylated laccase; acrylated lysyl oxidase; acrylated monoamine oxidase; acrylated xanthine oxidase; NADPH; and acrylated cytochrome P450 oxidase, wherein the acrylated enzyme retains at least some of its catalytic activity; and D-trehalose; wherein at least a portion of the at least one enzyme is immobilized in the hydrogel. In some embodiments the gel includes immobilized glucose and/or non-immobilized glucose. In some embodiments the gel includes an immobilized and/or a non-immobilized molecule that includes a glucose moiety or can be hydrolysed to a moiety of glucose.

An embodiment includes the composition according to any one of the preceding embodiments, wherein the at least one enzyme includes acrylated glucose oxidase, and where in a least a portion of the acrylated glucose oxidase is crosslinked to the hydrogel through covalent bonds.

An embodiment includes the composition according to any one of the preceding embodiments, wherein the at least one polymer building block includes polyethylene glycol.

An embodiment includes the composition according to any one of the preceding embodiments, wherein the hydrogel and the at least one enzyme immobilized in the hydrogel are lyophilized.

An embodiment includes methods of according at least one of the other embodiments comprising the steps of: providing the compositions of at least one of the other embodiments; and adding glutathione to the composition.

An embodiment includes the composition according to any one of the preceding embodiments, wherein the acrylated glucose oxidase is present in the range of about 1 mg/mL to about 50 mg/mL.

An embodiment includes the composition according to any one of the preceding embodiments, wherein the trehalose is present in the range of about 1 mg/mL to about 50 mg/mL.

An embodiment includes the composition according to any one of the preceding embodiments, wherein the glutathione is present in the range of about 2 mM to about 10 mM.

An embodiment includes the composition according to any one of the preceding embodiments, wherein glucose or other enzyme substrates present in the range of about 1 mM to about 25 mM.

An embodiment includes the composition according to any one of the preceding embodiments, wherein the concentration of crosslinked polymer falls in the range of about 5% to about 30%.

An embodiment includes a method for freeze-drying the composition of at least one of the other embodiments, comprising the steps of: providing a glucose oxidase-immobilized polymer hydrogel; and lyophilizing the glucose oxidase-immobilized polymer hydrogel immediately after gelation.

An embodiment includes the method according to any one of the preceding embodiments, further including the step of: storing the lyophilized glucose oxidase-immobilized polymer hydrogel at about or less than about −20° C.

An embodiment includes a method for culturing cells, comprising the steps of: providing a composition, the composition includes a hydrogel and a portion glucose oxidase, wherein at least some of the portion of glucose oxidase is immobilized in the hydrogel; and inoculating the combination with cells and/or spores. In some embodiments the cells are human cancer cells or animal cancer cells. In some embodiments the cells are bacteria cells or archeabacteria. In some embodiments the bacterial or archeabacterial cells are facultative anaerobes or obligate anaerobes. In some embodiments the inventive gels are inoculated with at least one cell or spore selected from the group consisting of: cancer cells, bacteria cells, archeabacteria cells, and bacterial spores.

An embodiment includes the method according to any one of the preceding embodiments, wherein the composition further includes between 1 mg/mL to 50 mg/mL trehalose.

An embodiment includes the method according to any one of the preceding embodiments, wherein the composition further includes between 2 mM to 10 mM glutathione.

An embodiment includes the method according to any one of the preceding embodiments in which the concentration of oxygen within and surrounding the composition is less than or equal to about 5%.

An embodiment includes the method according to any one of the preceding embodiments, wherein the cells are cancer cells.

An embodiment includes the method according to any one of the preceding embodiments, wherein the composition further includes a buffer and the glutathione is added to the buffer.

An embodiment includes the method according to any one of the preceding embodiments, wherein the composition further includes at least one compound that promotes cellular growth, selected from the group consisting of; sugars, sera, growth factors, vitamins, and signalling molecules.

An embodiment includes a device for creating a hypoxic gradient, comprising: at least one hydrogel according at least one of the other embodiments; and a channel slide having a first end and a second end, wherein the hydrogel is positioned at one end of the channel.

An embodiment includes the device according to any one of the preceding embodiments, wherein at least one hydrogel is placed at both the first end and the second end of the channel slide.

DESCRIPTION

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

Herein is disclosed an immobilized-enzyme strategy for inducing hypoxia within and surrounding a PEG-based hydrogel for in vitro cancer cell culture. Immobilization of $O_2$-consuming GOX within covalently crosslinked hydrogels provides an easy method to control solution $O_2$ tension without the use of external devices. Furthermore, GOX-immobilized hydrogels can be readily added to or removed from cell culture without disturbing cells. The crosslinked PEG hydrogel network also provides opportunities for immobilizing multiple proteins/enzymes or other functional molecules for other biomedical applications.

The flexibility and stability of the GOX-immobilized hypoxia-inducing hydrogel system is increased by the invention. GOX-immobilized hydrogels to which trehalose has been added are lyophilized for long-term storage. Trehalose is added into the gel formulation owing to its demonstrated ability to increase thermo-stability of proteins. Trehalose has been used as a soluble excipient to stabilize proteins under heat or lyophilization treatments. In the current invention, unmodified trehalose is used to preserve the activity of reconstituted freeze-dried GOX-immobilized hydrogels.

In the current invention, glutathione (GSH) is used instead of CAT in conjunction with GOX to sustain hypoxia. For each mole of CAT undergoing the reaction, one-half mole of oxygen is produced, which offsets the oxygen consumption ability of GOX. GSH however, reduced hydrogen peroxide to water, without molecular oxygen as a by-product, thereby solving this problem.

Figure 1A:
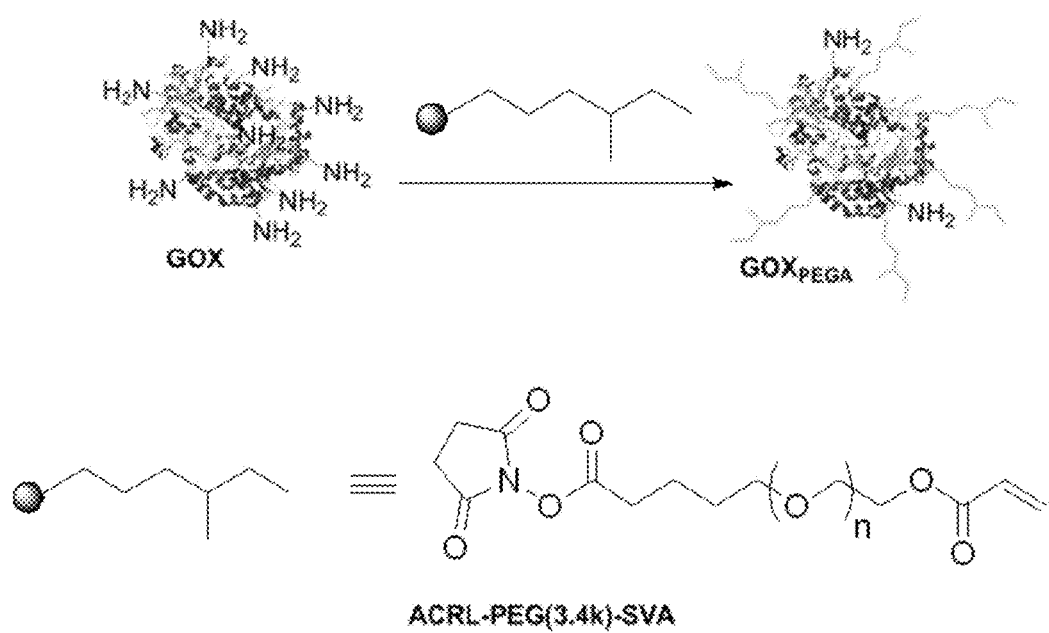
FIG. 1A. Brief Description: Reaction scheme of GOX modification using Acryl-PEG-SVA. Protein structure for GOX was obtained from the RCSB Protein Data Bank (PDB-ID, 3QVP).
Figure 1B:
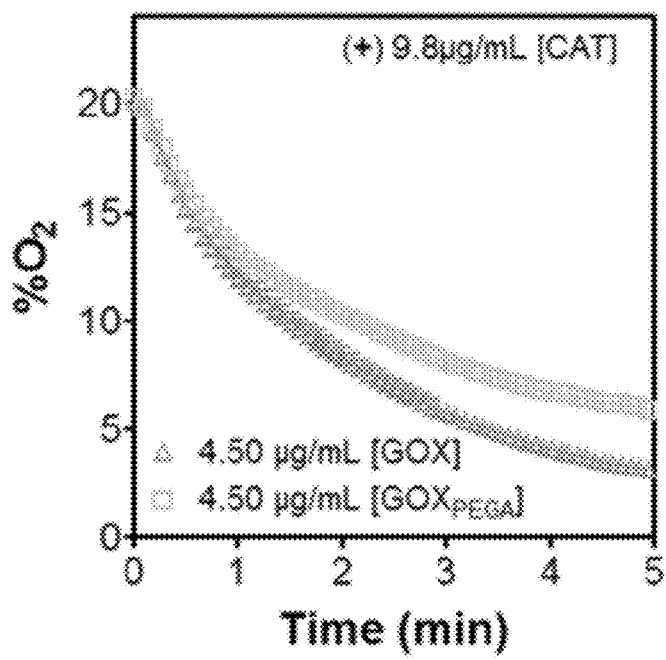
FIG. 1B. Brief Description: $O_2$ consumption profile using soluble GOX or $GOX_{PEGA}$, 9.8 µg/mL CAT, and 25 mM β-D-Glucose.
Figure 1C:
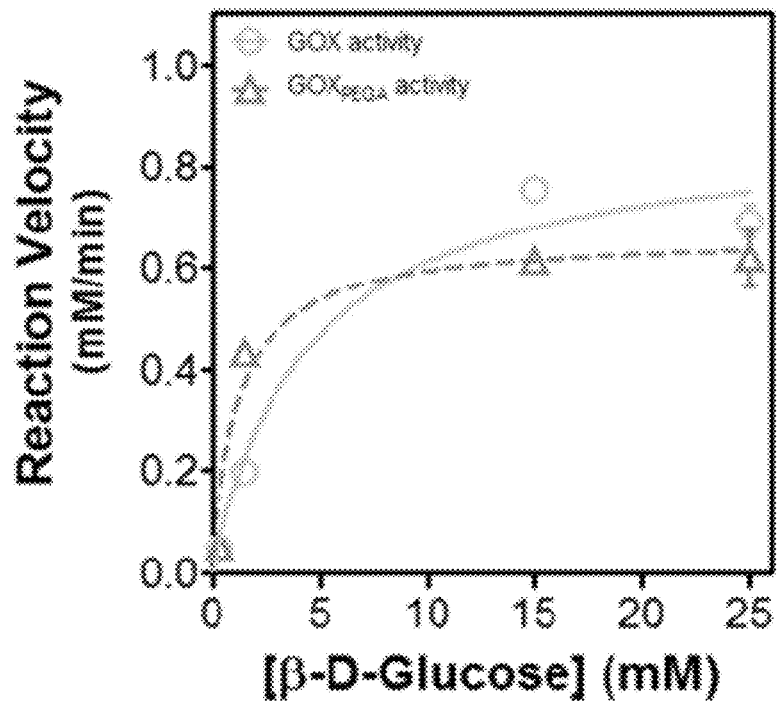
FIG. 1C. Brief Description: Reaction velocity of $O_2$ consumption by GOX or $GOX_{PEGA}$ as a function of substrate β-D-glucose concentration. Values were generated from using 0.260 µM GOX or $GOX_{PEGA}$ with 0.30-25 mM of 3-D-glucose. All reactions were carried out in pH 7.4 PBS with constant stirring at 25° C. (Mean±SEM, n≥3).

Fabrication of enzyme-immobilized hydrogels capable of inducing hypoxia is accomplished by functionalizing the primary amine groups on GOX with Acryl-PEG-SVA. TNBSA assay results showed an average of 93±1.7% (Mean±SEM, n=5) of the primary amines on enzyme surface were functionalized with Acryl-PEG. The acrylate moieties on the surface of Acryl-PEG-GOX (i.e., GOX$_{PEGA}$) permit its homopolymerization with PEGDA to afford enzyme-immobilized hydrogels. As shown in FIG. 1B., while un-modified GOX caused rapid $O_2$ reduction (from ~20% to ~3.2% in 5 min) in solution, the ability of GOX$_{PEGA}$ to consume $O_2$ was slightly hindered after Acryl-PEG-SVA modification (from ~20% to ~5.9% within 5 minutes). To quantify the impact of polymer modification on its enzyme activity, reaction velocities of GOX and GOX$_{PEGA}$ were measured and compared in FIG. 1C. Michaelis-Menten enzyme kinetic parameters were listed in Table 1. Maximum reaction velocity, $V_{max}$, was reduced for GOX$_{PEGA}$ to 0.664 mM min$^{-1}$, or approximately 75% of that for GOX (0.880 mM min$^{-1}$). Additionally, $K_m$, an estimate of the dissociation constant for enzyme and substrate, was also decreased for GOX$_{PEGA}$ at 1.173 mM versus GOX at 4.380 mM.

TABLE 1

Michaelis-Menten constants of GOX and GOX$_{PEGA}$

|  | $V_{max}$ (mM min$^{-1}$) | $K_m$ (mM) |
|---|---|---|
| GOX | 0.880 ± 0.045 | 4.380 ± 0.900 |
| GOX$_{PEGA}$ | 0.664 ± 0.033 | 1.173 ± 0.275 |

Figure 2A:
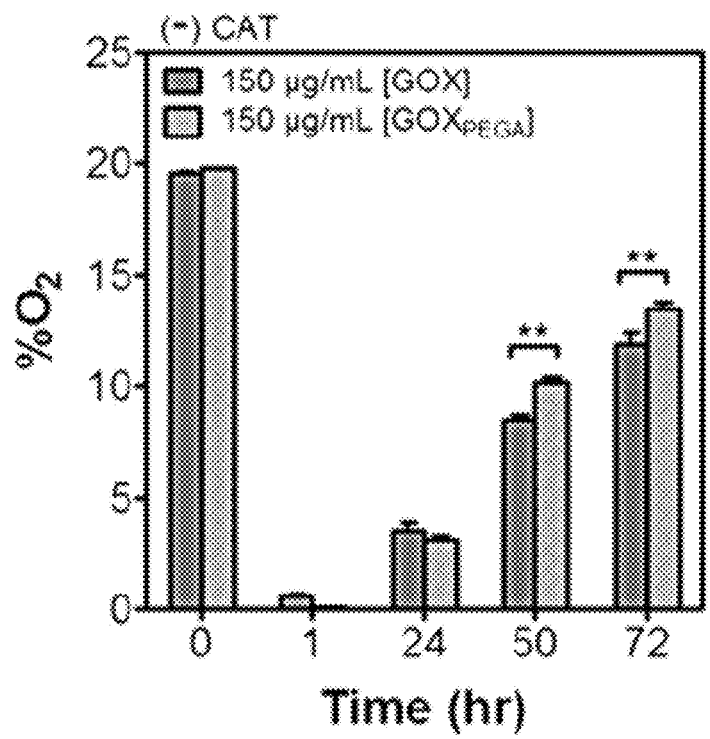
FIG. 2A. Brief description: Long term solution hypoxia induced by GOX or $GOX_{PEGA}$ in the absence of catalase (CAT).
Figure 2B:
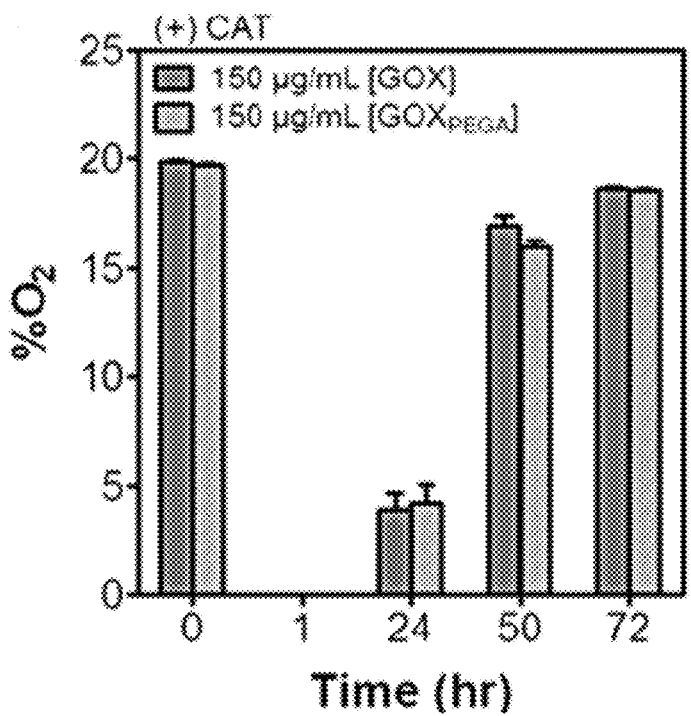
FIG. 2B. Brief description: Long term solution hypoxia induced by GOX or $GOX_{PEGA}$ in the presence of catalase (CAT). Between GOX and $GOX_{PEGA}$ groups, $O_2$ content was very similar for all time points. The addition of CAT did not affect $O_2$ content, which was below 5% in the first 24 hours for both GOX and $GOX_{PEGA}$.

To evaluate the ability of the enzyme system to maintain hypoxia, $O_2$ content measurements were carried out for 72 hours. FIG. 2. shows long term solution hypoxia induced by GOX or GOX$_{PEGA}$ in the absence (FIG. 2A.) and presence (FIG. 2B.) of CAT. Between GOX and GOX$_{PEGA}$ groups, $O_2$ content was very similar for all time points. Within the first 24 h, $O_2$ was maintained below 5% but gradually increased to ~13% by 72 hours (FIG. 2A.). The addition of CAT did not affect $O_2$ content, which was below 5% in the first 24 hours for both GOX and GOX$_{PEGA}$. The $O_2$ content in both conditions rose to ~16% and ~18% at 50 and 72 hours, respectively.

Figure 3A:
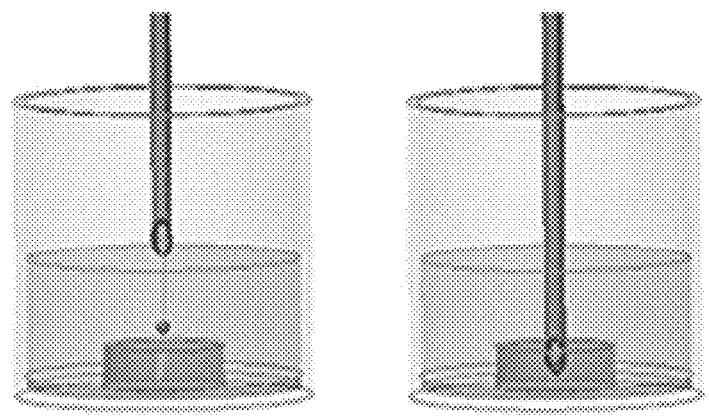
FIG. 3A. Brief Description: Schematic of $O_2$ measurement within and outside of a PEGDA hydrogel. The sensor probe was fully extended from the needle for measuring $O_2$ tension exterior to the hydrogel (left). To measure $O_2$ content at the interior of the hydrogel (right), the optic fiber was recessed within its needle housing to prevent damage of the gel matrix to the probe. After penetration the fiber was extended to the tip of the needle cannula so that it was exposed to the interior of the hydrogel.
Figure 3B:
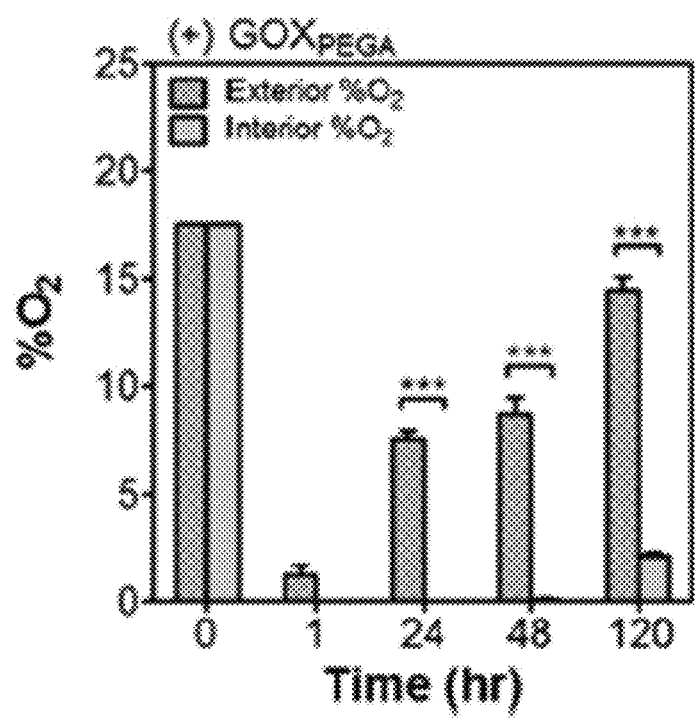
FIG. 3B. Brief Description: $O_2$ consumption at the interior or exterior of GOX-immobilized hydrogels (120 µL of 8 wt % PEGDA gel with 4 mg/mL $GOX_{PEGA}$). (***p<0.001. Mean±SEM, n≥3).
Figure 4:
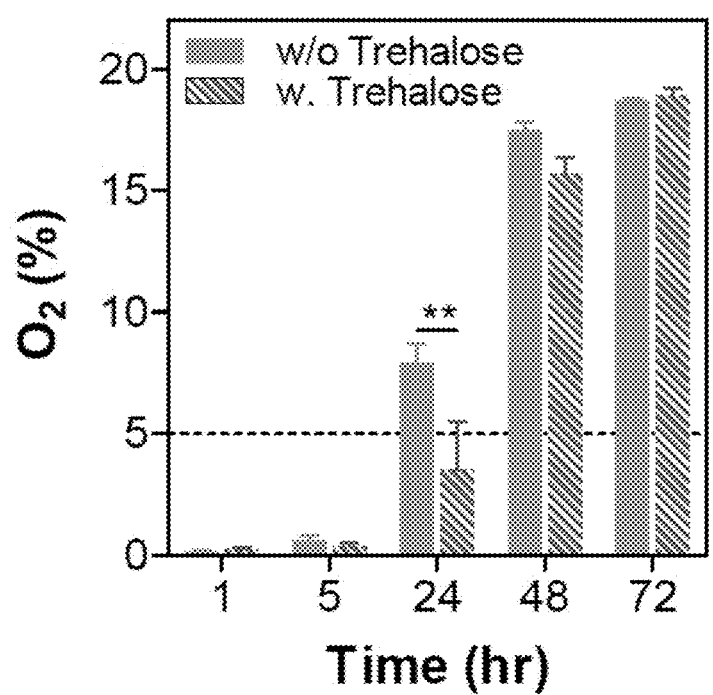
FIG. 4. Brief Description: Effect of trehalose on solution hypoxia induced by freeze-dried GOX immobilized hydrogels. Trehalose was added at 3 mg/ml during gelation. Hydrogels (30 µl) were polymerized with 15 wt % $PEGDA_{2kDa}$, 0.8 mg/ml $GOX_{PEGA}$, and 1 mM LAP.
Figure 5A:
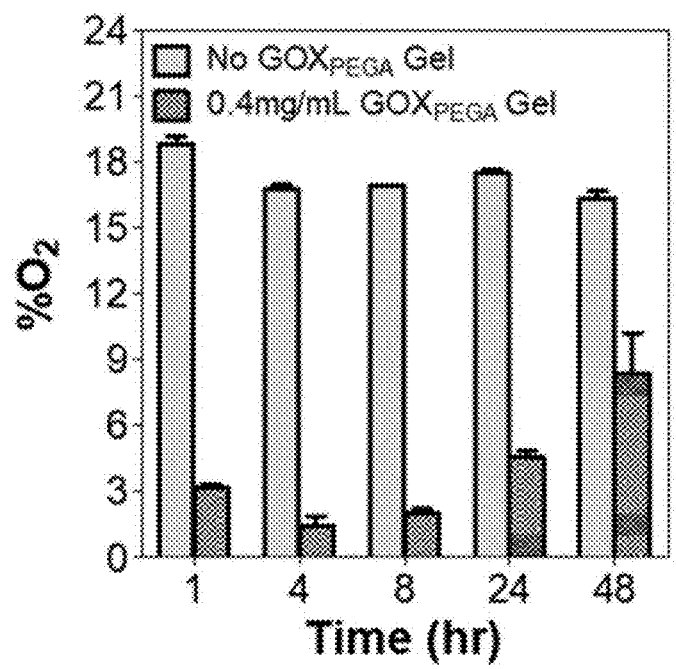
FIG. 5A. Brief Description: Percent $O_2$ measured as a function of time for a $GOX_{PEGA}$ hydrogel in an ibidi channel slide and a control with no hydrogel. The hydrogel is 20 total volume formed by 15% weight PEGDA with 0.4 mg/mL $GOX_{PEGA}$. (***p<0.001. Mean±SEM, n≥3).
Figure 5B:
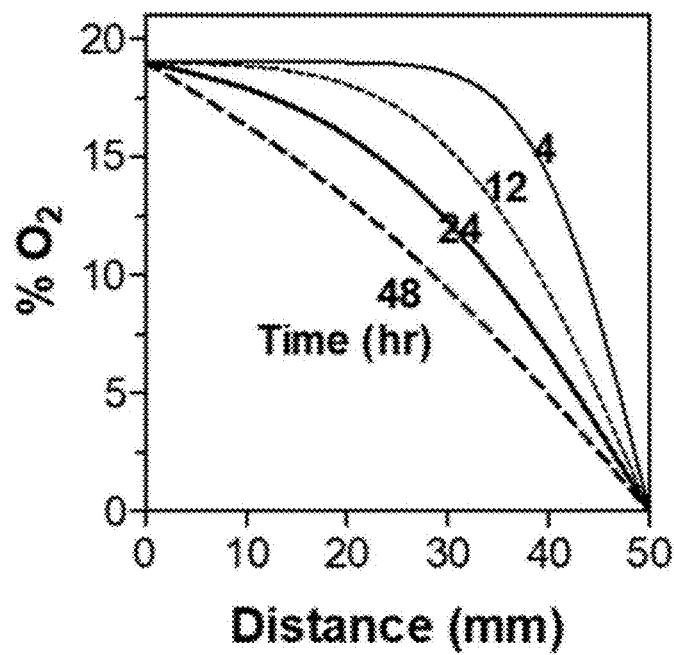
FIG. 5B. Brief Description: Empirical mesh-modeling of Ficks 1D-diffusion equation for $O_2$ concentration as a function of time and distance across a channel in a 50 mm channel slide. The boundaries were set to normoxia (19% $O_2$) on one end of the channel and 3% at the other.
Figure 5C:
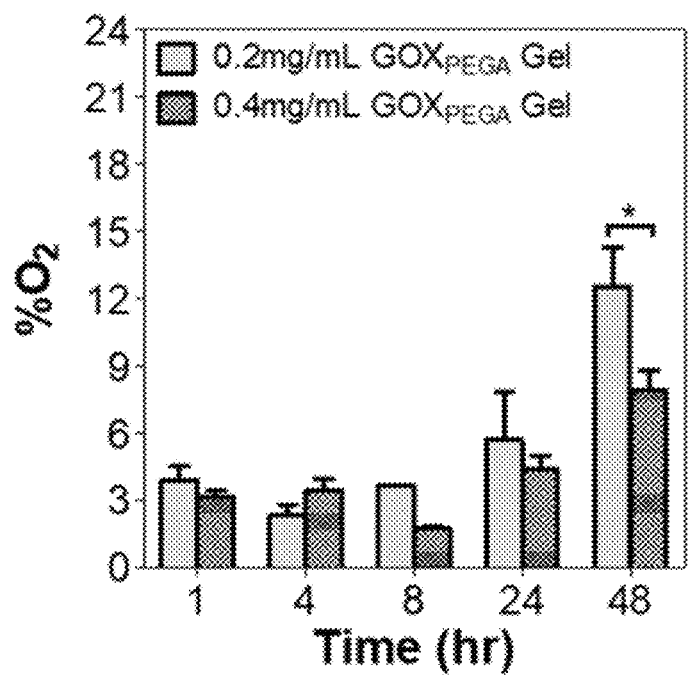
FIG. 5C. Brief Description: Percent $O_2$ measured as a function of time for a $GOX_{PEGA}$ hydrogels in an ibidi channel slide with a control lacking a hydrogel. The hydrogel is 20 µL total volume formed by 15% weight PEGDA with either 0.2 or 0.4 mg/mL $GOX_{PEGA}$ (one hydrogel per reservoir). (*p<0.05. Mean±SEM, n≥3).
Figure 5D:
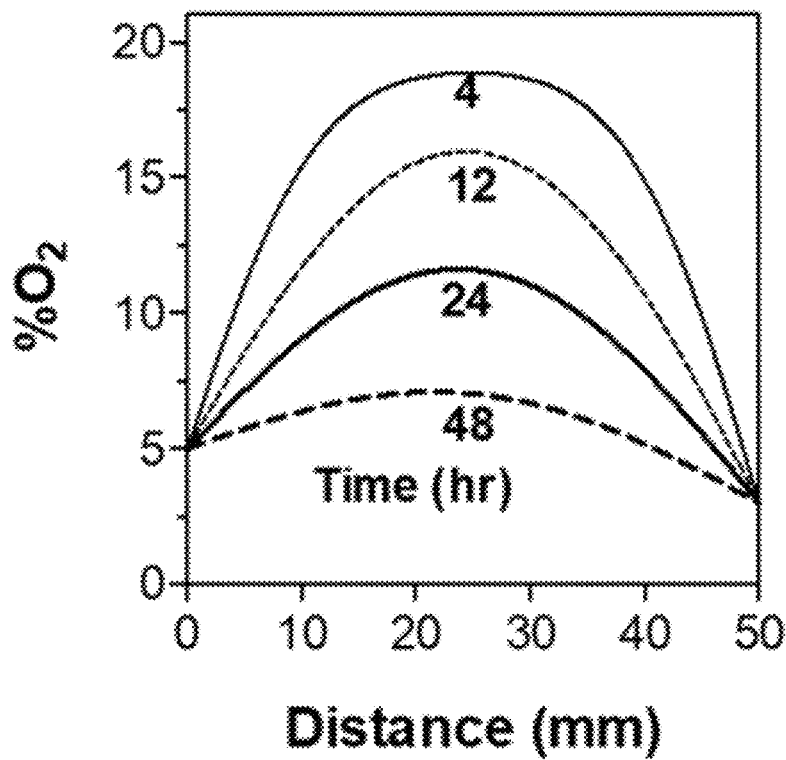
FIG. 5D. Brief Description: Empirical mesh-modeling of Ficks 1D-diffusion equation for $O_2$ concentration as a function of time and distance across a channel in a 50 mm channel slide. The boundaries were set to 5% $O_2$ on one end of the channel and 3% at the other.

GOX$_{PEGA}$ was covalently immobilized within PEGDA hydrogels to provide a simple method for inducing solution hypoxia. The ability of the immobilized enzyme to reduce $O_2$ in the surrounding solution and within the gel was measured with a needle type optical probe as shown in FIG. 3A. With the needle type $O_2$ probe, it was possible to measure $O_2$ content outside (left panel) or inside (right panel) the GOX$_{PEGA}$ immobilized hydrogels (FIG. 3B.). Control experiments using hydrogels without enzyme immobilization (i.e., (-) GOX$_{PEGA}$) showed that $O_2$ content remained close to normoxia (17-20% $O_2$). Furthermore, there was no significant difference between $O_2$ content within or outside of the enzyme-free hydrogels. With the use of GOX$_{PEGA}$ immobilized PEG hydrogels, however, there was a rapid drop in the 'exterior' (i.e., outside of the GOX$_{PEGA}$ immobilized hydrogel) $O_2$ tension within one hour, a level similar to that with soluble enzyme (FIG. 2A.). $O_2$ tension was roughly at ~8% $O_2$ for 48 hours in solution with the GOX$_{PEGA}$ hydrogels. Conversely the $O_2$ tension within the GOX$_{PEGA}$ hydrogel quickly reached and maintained near anoxia (~0% $O_2$) for 48 hours. The $O_2$ tension at the gel exterior had increased to ~15% by 120 hours, while that in the gel interior was still below 2%.

In one embodiment of the current invention, glucose oxidase (GOX) is acrylated and copolymerized with poly (ethylene glycol)-diacrylate (PEGDA) in the presence of trehalose to form GOX-immobilized PEG-based hydrogels.

In another embodiment, hypoxia gradients are created by placing the enzyme-immobilized gels into a channel slide.

In still another embodiment, glutathione is added to the buffer solution so as to extend hypoxia within the hydrogel for at least 72 hours.

In yet another embodiment, the enzyme-immobilized hydrogels are lyophilized for longer term storage.

In another embodiment, the enzyme-immobilized hydrogels are used for the cancer cell studies.

EXPERIMENTAL

Materials and Methods

Linear PEG (Mn=2 kDa) was purchased from Sigma-Aldrich. Glucose oxidase (0243-500KU) and catalase (LS001847) were purchased from Amresco and Worthington Biochemical, respectively. Acrylate-PEG-succinimidyl valerate (Acryl-PEG-SVA, MW 3400 Da) was obtained from Laysan Bio Inc. Zeba Spin Desalting Columns (7 K MWCO), 2,4,6-trinitrobenzene sulfonic acid (TNBSA), and β-D-glucose were purchased from Thermo Scientific. Penicillin-streptomycin, antibiotic-antimycotics, fetal bovine serum (FBS), Roswell Park Memorial Institute media (RPMI), and Dulbecco's modified Eagle's medium (DMEM) were acquired from Life Technologies. HEPES and Dulbecco's phosphate-buffered saline (DPBS) were purchased from Lonza. Membrane culture plate inserts (PIXP012-50) were purchased from EMD Millipore. Trypan blue and AlamarBlue® reagents were purchased from Mediatech and Fisher Scientific, respectively.

Linear PEG (Mn: 2 kDa) was purchased from Sigma-Aldrich. Glucose oxidase (0243-500KU) and acrylate-PEG-succinimidyl valerate (Acryl-PEG-SVA) were obtained from Laysan Bio and Amresco, respectively. β-D-glucose and glutathione were purchased from Thermo Scientific. D-trehalose was acquired from Acros Organic. Penicillin-streptomycin, antibiotic-antimycotics, fetal bovine serum (FBS), and Dulbecco's modified Eagle's medium (DMEM) were acquired from Life Technologies. HEPES and Dulbecco's phosphate-buffered saline (DPBS) were purchased from Lonza. Membrane culture plate inserts (PIXP-012-50) were purchased from EMD Millipore. Ellman and AlamarBlue® reagents were purchased from Fisher Scientific.

Example 1

Macromer Synthesis and Characterization

PEG-diacrylate (PEGDA) is synthesized according to an established protocol and characterized with $^1$H NMR (Bruker 500). The degree of PEGDA functionalization is around 89% (FIG. S1). Photoinitiator lithium aryl phosphonate (LAP) is synthesized as described elsewhere. To facilitate enzyme immobilization within hydrogels, glucose oxidase is acrylated using Acryl-PEG-SVA using the method according to Choi et al. Briefly, the enzyme is first dissolved at 20 mg/mL in PBS supplemented with 2 mM EDTA (pH 8.5) and 50 mM sodium carbonate. Acryl-PEG-SVA is added in 200× molar excess to enzyme concentration and the reaction proceeds at room temperature for 2 hours with stirring. During the reaction, primary amines on the surface of the enzyme react with SVA groups to afford PEG-acrylate (PEGA)-modified GOX ($GOX_{PEGA}$). Unreacted macromers are removed using size exclusion chromatography columns (Zeba Spin Desalting column). Un-modified GOX at the same concentration is also passed through the columns and used as a control to account for any loss/entrapment of enzyme within the columns. Following synthesis, both GOX and $GOX_{PEGA}$ are assayed using TNBSA assay to determine the degree of PEGA functionalization. For each assay, enzyme samples are diluted to 30-35 µg/mL. A series of lysine hydrochloride solutions (0-10 µg/mL, 200 µL/well) are used as standards. 100 µL of 0.01% TNBSA reagent is added into wells of a 96-well plate, which is sealed and incubated at 37° C. for 2 hours, followed by cooling for 5 minutes. Absorbance at 335 nm is measured using a microplate reader (SynergyHT BioTek). The degree of PEGA functionalization on GOX is determined as the concentration of remaining amine groups on $GOX_{PEGA}$ over that of the un-modified GOX.

Example 2

Characterization of Enzymatic Activity of $GOX_{PEGA}$

To examine the enzyme activity, $O_2$ consumption in the presence of the enzyme and glucose is quantified. The changes in $O_2$ content over time in the presence of GOX or $GOX_{PEGA}$ ($V_o = \Delta [O_2]/\Delta Time$) is defined as the reaction velocity. The enzyme is dissolved PBS (pH 7.4) at 0.13 µM in a 2 mL microtube with constant stirring at 25° C. The $O_2$ consumption reactions are carried out under ambient air with constant $O_2$ diffusion from the air to mimic actual cell culture conditions. Stock β-D-glucose solution is injected at the start of every measurement to give starting concentrations of 0.30-25 mM $[S]_f$. Dissolved $O_2$ concentration is monitored for 3 minutes using an $O_2$ probe and meter (Microx4, PreSens; see Example 6). $O_2$ contents are plotted as a function of time and the initial linear portion of the curve was used for $V_o$ calculation (change in substrate concentration over time). Non-linear regression analysis and curve fitting is applied to paired $V_o$ and $[S]_f$ using the equation $V_o = V_{max}[S]/(K_m+[S])$. In the equation, $V_{max}$ is the theoretical maximum enzyme reaction velocity and $K_m$ is the Michaelis-Menten constant, the equilibrium dissociation constant (i.e., affinity) for the enzyme and the substrate.

Example 3

Synthesis and Characterization of Enzyme-Immobilized Hydrogels

All macromer solutions are sterilized by passing through 0.22 µm syringe filters. PEGDA hydrogels (15 wt %) are polymerized aseptically through radical mediated photopolymerization in the absence or presence of $GOX_{PEGA}$ monomer (6 mg/mL), and LAP (1 mM) as the photoinitiator. 60 µL gels are injected between two glass slides separated by Teflon spacers (2 mm) and gelation is initiated with a UV lamp (365 nm, 5 mW/cm$^2$, 2 minutes exposure). Following photopolymerization, hydrogels (~3.1 mm dia.×2 mm thickness) are incubated in DPBS for 24 hours at 37° C.

Example 4

Synthesis of Trehalose-Stabilized Enzyme-Immobilized Hydrogels

Trehalose is added at 3 mg/ml during gelation. Hydrogels (30 µl) are polymerized with 15 wt % $PEGDA_{2kDa}$, 0.8 mg/ml $GOX_{PEGA}$, and 1 mM LAP. All reactions are carried out at room temperature in DPBS with 25 mM β-D-Glucose and HEPES.

Example 5

Effect of Solution GSH Content on Sustained Hypoxia

Figure 6A:
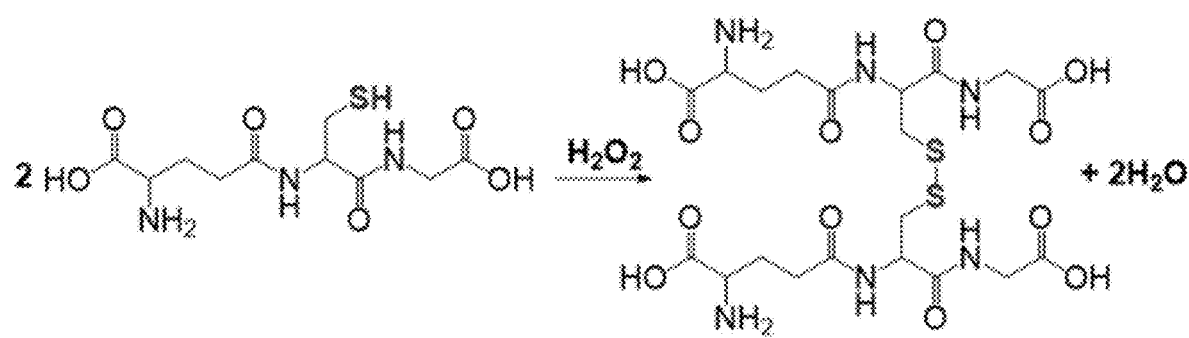
FIG. 6A. Brief Description: Oxidation reaction mechanism of glutathione (GSH) by $H_2O_2$.
Figure 6B:
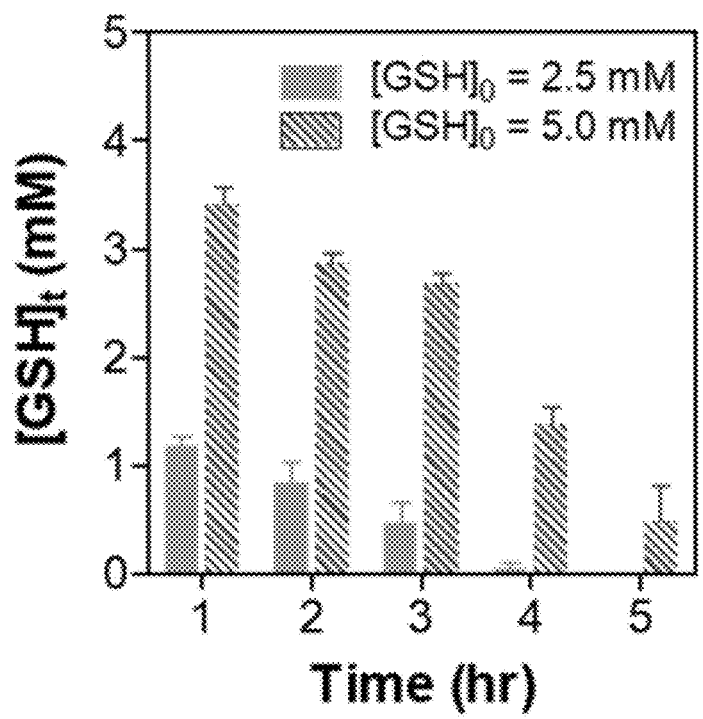
FIG. 6B. Brief Description: GSH consumption in the presence of GOX gel.
Figure 6C:
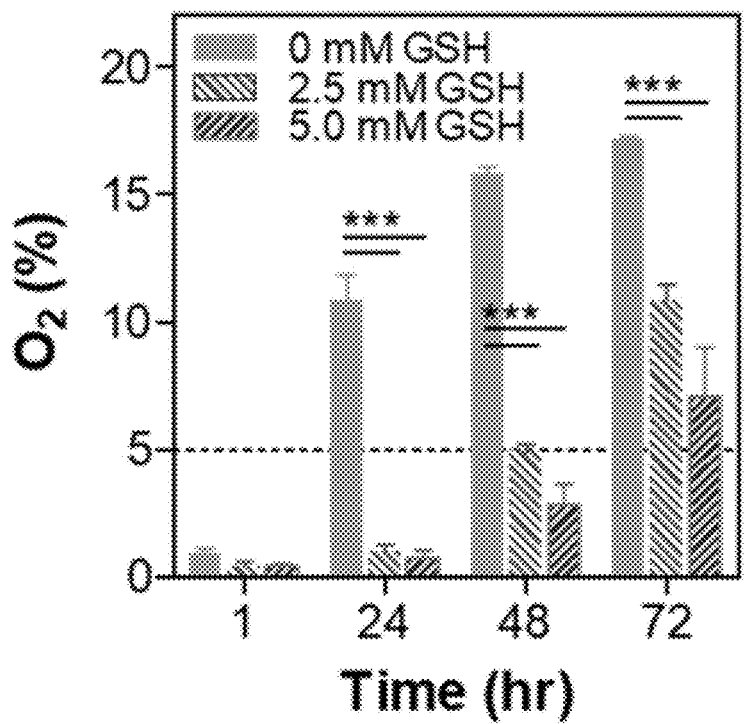
FIG. 6C. Brief Description: Solution hypoxia prolonged by GSH. Hydrogels (30 µl) are polymerized with 15 wt % $PEGDA_{2kDa}$, 0.2 mg/ml $GOX_{PEGA}$, 3 mg/ml trehalose and 1 mM LAP. (***p<0.001. Mean±SEM, n≥3).
Figure 7A:
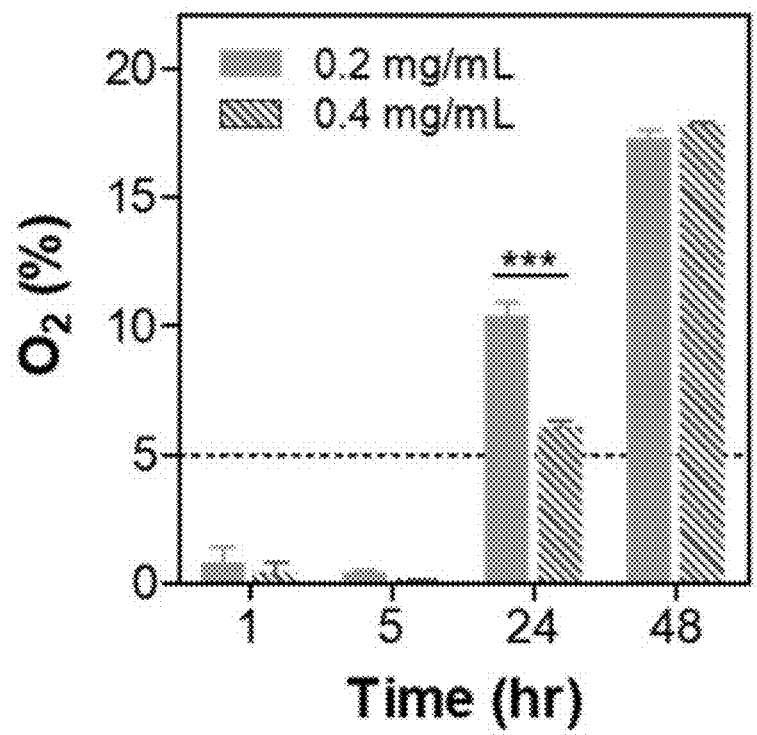
FIG. 7A. Brief Description: Solution hypoxia induced by freshly prepared GOX-immobilized hydrogels. Hydrogels (30 µl) are polymerized with 15 wt % $PEGDA_{2kDa}$ and 1 mM LAP. All reactions are carried out at room temperature in DPBS with 25 mM β-D-Glucose and HEPES. (***p<0.001. Mean±SEM, n≥3).
Figure 7B:
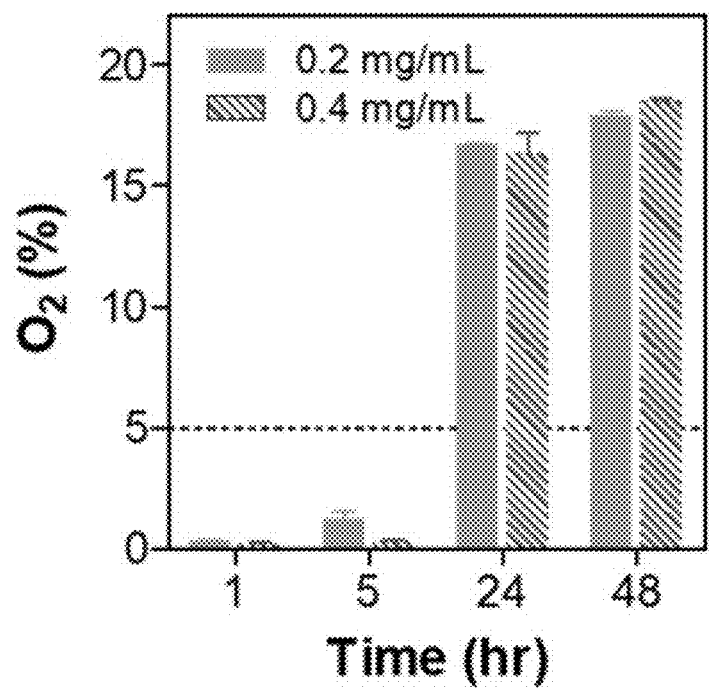
FIG. 7B. Brief Description: Solution hypoxia induced by freeze-dried GOX-immobilized hydrogels. Freeze-dried gels are reconstituted in 1 mL DPBS overnight. Hydrogels (30 µl) are polymerized with 15 wt % $PEGDA_{2kDa}$ and 1 mM LAP. All reactions are carried out at room temperature in DPBS with 25 mM β-D-Glucose and HEPES.
Figure 8A:
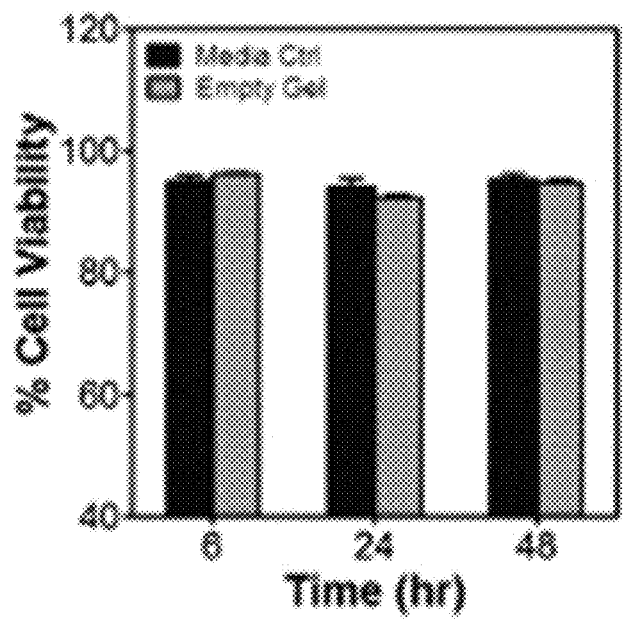
FIG. 8A. Brief Description: Cytocompatibility of enzyme-free (i.e., PEGDA only) hydrogels. Molm14 cell viability is maintained above 95% over the course of 48 hours in the presence of an enzyme-free PEGDA hydrogel.
Figure 8B:
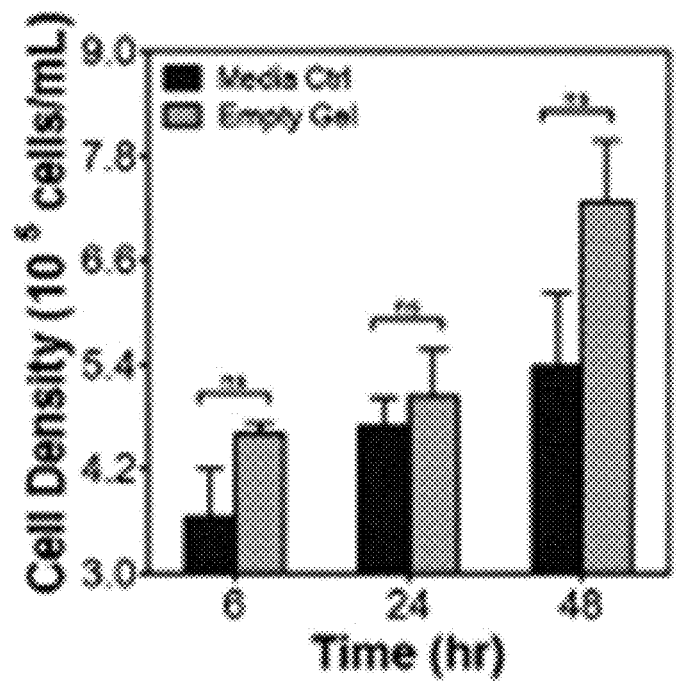
FIG. 8B. Brief Description: The Molm14 cells proliferate over time, as indicated by steady increase in cell density.
Figure 8C:
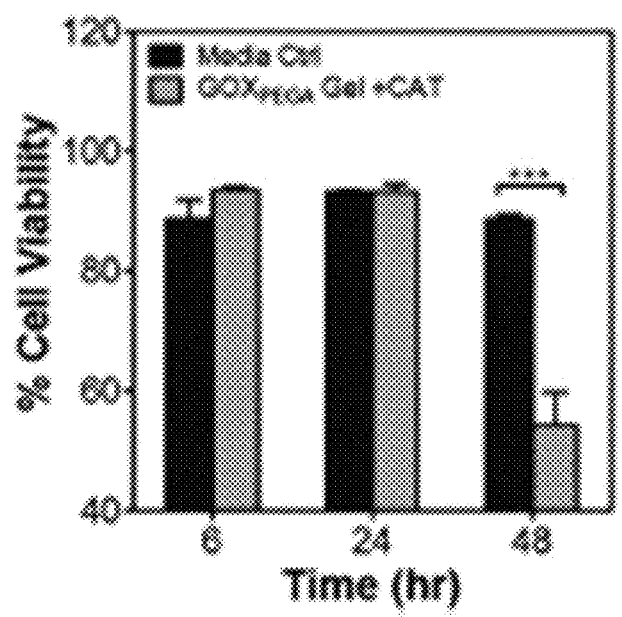
FIG. 8C. Brief Description: When a $GOX_{PEGA}$ gel is placed together with Molm14 cells (with media-supplemented CAT), cell viability in the initial 24 hours is comparable to that in the media-only control (around 90%).
Figure 8D:
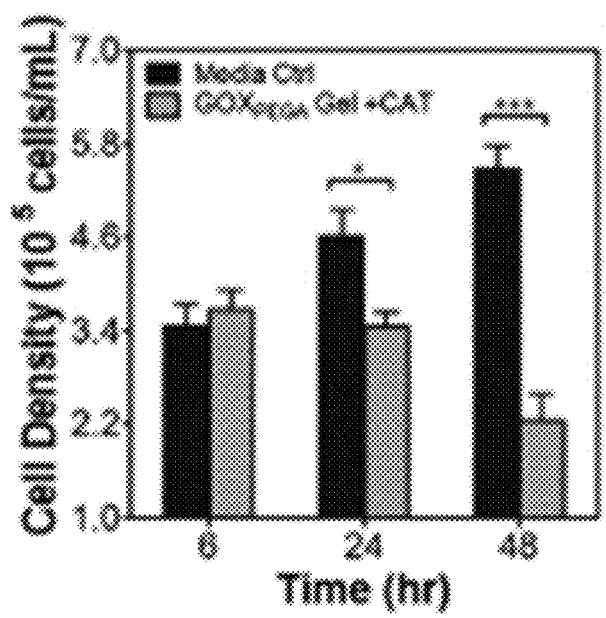
FIG. 8D. Brief Description: After 48 hours of in vitro culture, Molm14 cell viability declined sharply to ~55%. In addition to the decreased cell viability after 48 hours, a similar trend can be seen with cell density over time. There is no significant difference in cell density between the control and experimental group at 6 hours (i.e., ~3.6×10$^5$ cells/mL). By 48 hours the Molm14 cell density in the media-only control group had increased to ~5.5×10$^5$ cells/mL, whereas the Molm14 cell density in the GOX-immobilized hydrogel group decreased significantly to ~2.2×10$^5$ cells/mL.
Figure 9A:
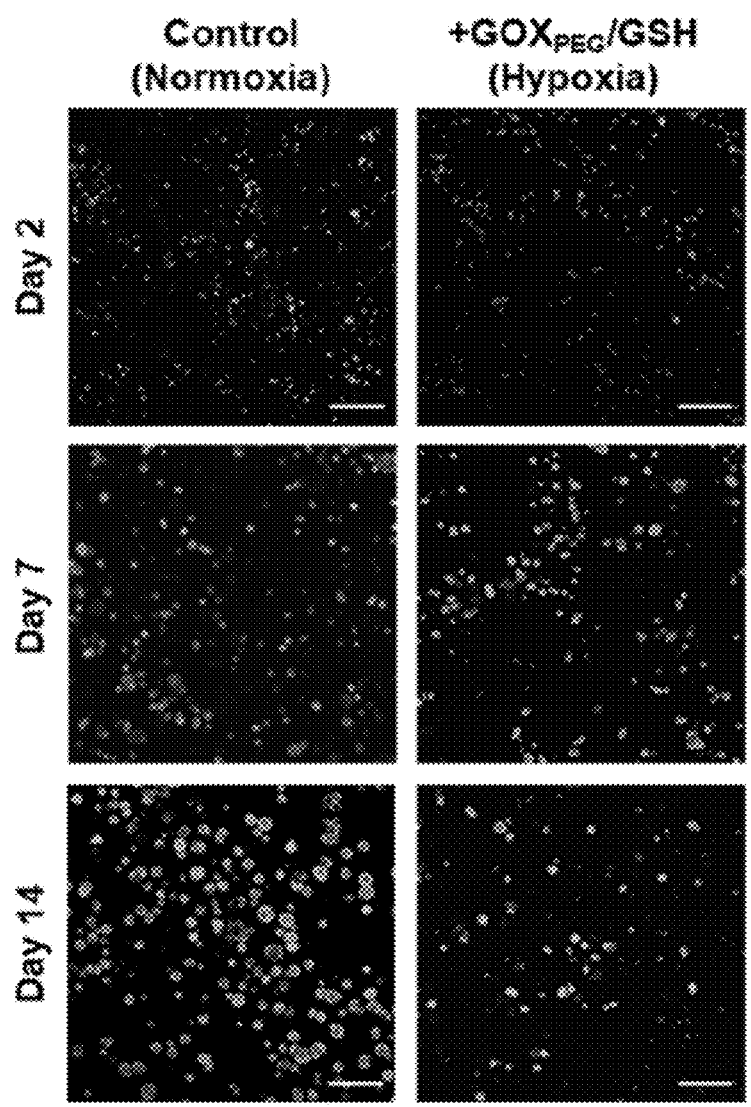
FIG. 9A. Brief Description: Effect of enzyme induced hypoxia on cell fate of COLO 357 cell-laden gels. COLO-357 cell morphology is shown under normoxia (control) or hypoxia.
Figure 9B:
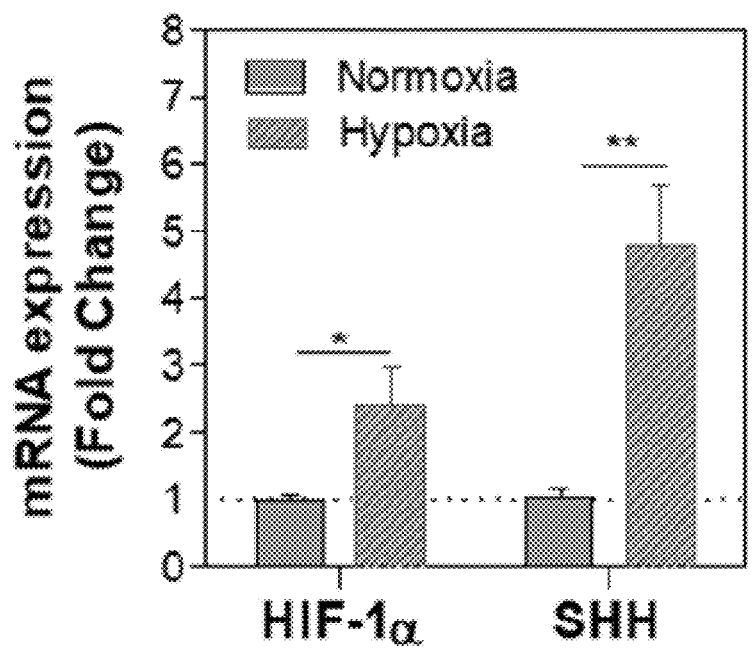
FIG. 9B. Brief Description: mRNA expression Ribosomal 18s as the housekeeping gene.
Figure 9C:
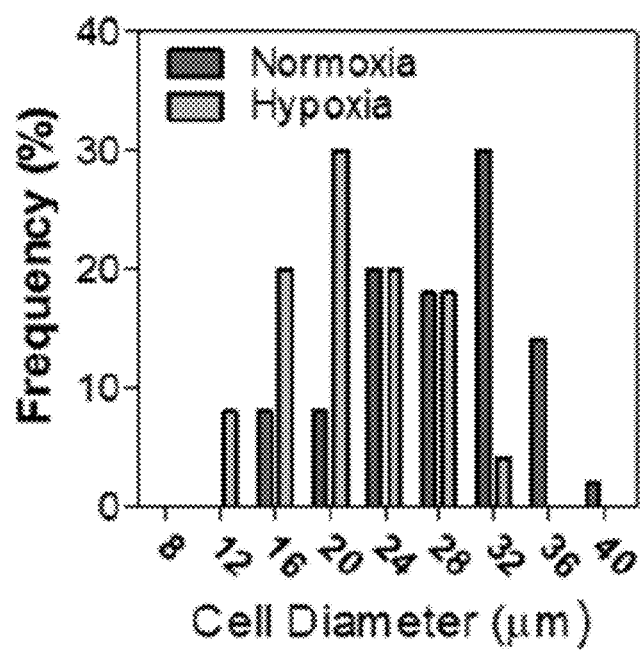
FIG. 9C. Brief Description: Cell size distribution. Hypoxia is induced by 30 µl hydrogels polymerized with 15 wt % $PEGDA_{2kDa}$, 0.2 mg/ml $GOX_{PEGA}$, 3 mg/ml trehalose and 1 mM LAP. GOX$_{PEGA}$ gel is placed in the same well as the cell-laden hydrogel (*p<0.05, **p<0.01. Mean±SEM, n≥3).

To mitigate the adverse effect of the accumulated $H_2O_2$, glutathione (GSH) is added to the buffer. GSH is a strong reducing agent for reactive oxygen species, such as $H_2O_2$. Specifically, GSH reduces $H_2O_2$ into water without producing additional oxygen as does catalase. Indeed, when GSH is added to the solution at 2.5 mM or 5 mM, the oxygen contents in the buffers remain at around 2-3% for 24 hours (FIG. 6C). By 48-hour measurements, the oxygen contents in the solutions increases to ~6% and ~3.5% for solution added with 2.5 mM and 5.0 mM of GSH, respectively. By 72-hour measurement, the solution oxygen level remains at around 5% for buffer added with 5 mM GSH (FIG. 6C).

Example 6

Measurement of $O_2$ Concentration $O_2$ concentration in solution is measured with a dipping-type $O_2$ sensor (Microx4, PreSens). For solution based measurements, the probe is extended to ~2 mm above the bottom of the 24 well plate or 1 mm above the gel (~2 mm from the liquid-air interface). To measure the $H_2O_2$ produced during the reactions, 10 μL aliquots of the solutions are collected and quantified with a Quantichrom Peroxide Assay Kit following the manufacturer's protocol (BioAssay Systems).

Example 7

Establishing Hypoxia Gradients Using Enzyme Immobilized Hydrogels

Specialized channel slides are available from ibidi (GmbH, Munich, Germany, catalogue number 80111, μ-Slide-1). The slides contain two reservoirs connected by a 50 mm channel. $O_2$ diffusion within the channel is simulated numerically with a finite difference approximation of a one-dimensional diffusion equation. For boundary conditions, $O_2$ concentration is held constant at each end of the channel (i.e., in the reservoirs) to represent either $O_2$-sinks or $O_2$-sources. For initial conditioning within the channel, $O_2$ concentration is assumed to be normoxic (about 19% $O_2$) at the left reservoir and 3% at the right at 0 hours of the simulation. At 4 hours of simulated $O_2$ diffusion in the channel, normoxic concentration of $O_2$ are predicted from the 0-35 mm mark, while from the 35-50 mm mark, $O_2$ concentration drops from 18.1% to 3%. At 12 hours, from the 25-50 mm mark, $O_2$ concentration decreases monotonically from 18.1% to 3%. By 36 hours, $O_2$ concentration drops from 17.3% to 3% at the 10-50 mm marks. Finally, at 48 hours, a channel-wide gradient from 19% to 3% $O_2$ is predicted. In contrast, a second simulation using 5% and 3% $O_2$ concentration in the two reservoirs of the channel slide gives a peak $O_2$ concentration at the center of the channel (from the 15-35 mm marks) with monotonically decreasing values to either the left or the right.

Hydrogels with either 0.2 or 0.4 mg/mL $GOX_{PEGA}$ (20 μL volume) are used within the reservoirs of the channel slide to generate $O_2$ consumption over time. FIG. 5 shows measured $O_2$ values as well as results of the numerical simulations of $O_2$ gradients within the channel.

Example 8

Cell Culture and Viability Assays Using Molm 14 Cells

A suspension cell type, human acute myeloid leukemia (AML) cells Molm14, are commercially available through the Leibniz Institute, German Collection of Microorganisms and Cell Cultures. Cells are maintained in RPMI media supplemented with 10% fetal bovine serum (FBS) and 1% penicillin-streptomycin 25 mM HEPES, and 25 mM β-D-Glucose. 400,000 cells/mL of Molm14 cells are seeded per well in non-treated 24 well plates. $GOX_{PEGA}$ gels (15 wt % PEGDA, 6 mg/mL $GOX_{PEGA}$, 60 μL per gel) are added to half of the wells (one gel per well) containing 0.54 mg/mL catalase. Remaining wells are placed with gels without immobilized enzyme. In vitro $O_2$ concentration is measured 1 mm above the hydrogel with a dipping-type $O_2$ sensor (PreSens). Molm14 cell viability and density are characterized by tryphan blue staining and counting with a hemocytometer. The survival and progression of these cells, just like many other cancer cell types, are significantly affected by $O_2$ tension. $GOX_{PEGA}$ immobilized hydrogels were prepared and added to anchorage-independent Molm14 cells cultured directly. Solution hypoxia is rapidly induced and maintained below 5% $O_2$ from 6 to 24 h. By 48 h, however, $O_2$ concentration rises to near normoxia (17-20% $O_2$).

RNA isolation is carried out using NucleoSpin RNA II kit (Clontech). Briefly, 600 μL of lysis buffer is added to each well containing cells. Cell lysates are snap frozen and stored in 80° C. until assay. After thawing the lysates, 600 μL of 70% RNase free ethanol is added, pipetted vigorously, and then run through NucleoSpin RNA columns. After desalting/purification steps, RNA is eluted with DNase/RNase-free $H_2O$ and quantified by spectroscopy (NanoDrop 2000, Thermo Scientific). Isolated RNA is stored at −80° C. Complementary DNA is generated from the isolated total RNA by using PrimeScript RT reagent kit (Clontech, TaKaRa). Gene expression is analyzed by real time quantitative PCR using SYBR Premix Ex Taq II Kit (Clontech, TaKaRa). The kit components, cDNA, and primers are mixed in a PCR plate and analyzed on a 7500 Fast Real-Time PCR machine (Applied Biosystems). Thermocycling parameters were one cycle at 95° C. for 30 s, followed by 95° C. for 3 s, 60° C. for 30 s, and repeated for 45 cycles. Gene expression results are analyzed using $2^{-\Delta\Delta CT}$ methodology. For each experimental condition, cycle count is first standardized to ribosomal 18S housekeeping gene (ΔCT level) and then normalized with respect to the media control group for that specific time point (ΔΔCT level; media control values are set as one-fold).

The expression of hypoxia associated gene carbonic anhydrase 9 (CA9) in Molm14 cells is evaluated at 6 and 24 hours of culture in the presence of a GOX-immobilized hydrogel. Enzyme-induced hypoxia increased the expression of CA9 significantly compared with control groups (~3-fold and ~10-fold higher at 6 and 24 hours of culture, respectively).

Example 9

Cell Culture and Viability Assays Using Huh7 Cells

Adherent cell type human hepatocarcinoma cells (Huh7) are grown in high glucose DMEM supplemented with 10% FBS, 1% antibiotic antimycotics, and 25 mM HEPES. Cells are seeded on treated 24 well plates with 1 mL per well of cell suspension (60,000 cells/mL) and allowed to grow/spread for 48 h prior to the onset of the experiments, at which time (labeled as 0 h) culture media is refreshed in all wells. At the onset of the experiment, membrane inserts containing $GOX_{PEGA}$ gels are placed in the wells and the medium is supplemented with 0.54 mg/mL CAT. Half of the wells only have media refreshed and are used as control groups for the experiment (no enzyme added). Alamar-Blue® reagent (10× dilution in media) is used for assaying metabolic activity of Huh7 cells. After a 90 min incubation, 200 μL from each well is transferred to a clear 96-well microplate and read for fluorescence (excitation/emission: 560/590 nm). $GOX_{PEGA}$-immobilized hydrogels are placed in a standard transwell device and co-cultured with the cells adhered to the surface of a multi-well plate. The purpose of using a transwell device is to prevent direct contact of the gel with the cells, which could mechanically disrupt cell attachment. The $O_2$ profile development was similar to that for Molm14 cells. Low $O_2$ concentration was reached quickly and maintained up to 24 h. By 48 h, the $O_2$ content had returned to almost normoxia. RNA isolation and analysis is carried out as described in Example 8. The expression of carbonic anhydrase 9 (CA9) and lysyl oxidase (LOX) is examined after the cells are exposed to the enzyme-immobilized hydrogel (Note: no detectable LOX expression was found in Molm14 cells). In selected groups, $CoCl_2$ was added as another control for chemically stimulated hypoxic response. $CoCl_2$ failed to upregulate CA9 expression in the first 24 hours. After the same period of time in culture, the use of $GOX_{PEGA}$ gels+CAT led to a ~20-fold increase in CA9 expression in Huh7 cells. After 48 hours, the addition of $CoCl_2$ caused ~15-fold upregulation in CA9 mRNA expression, which was much lower than that induced by the enzyme-immobilized hydrogel group (~80-fold higher). In Huh7 cells, LOX mRNA expression was upregulated only in cells co-cultured with a $GOX_{PEGA}$ gel (~2.5 fold, FIG. S4). The addition of $CoCl_2$ did not increase the expression of LOX in Huh7 cells.

Example 10

COLO-357, a pancreatic cancer cell line, was maintained in high glucose DMEM supplemented with 10% FBS, 1% antibiotic antimycotics, and 25 mM HEPES. Cells are encapsulated in gelatin-norbornene (GelNB)-thiolated hyaluronic acid (THA) hybrid hydrogels via thiol-norbornene photopolymerization as described previously. Cell-laden hydrogel is cultured in the presence of GOX-immobilized hydrogel for 2 weeks with periodical exchange of GOX-immobilized gel to maintain solution hypoxia.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

APPENDIX

References

1. Allen, C. B., Schneider, B. K., White, C. W., 2001. Limitations to oxygen diffusion and equilibration in in vitro cell exposure systems in hyperoxia and hypoxia. American journal of physiology. Lung Cell. Mol. Physiol. 281, L1021-1027.
2. An, W. G., Kanekal, M., Simon, M. C., Maltepe, E., Blagosklonny, M. V., Neckers, L. M., 1998. Stabilization of wild-type p53 by hypoxia-inducible factor 1alpha. Nature 392, 405-408.
3. Askoxylakis, V., Millonig, G., Wirkner, U., Schwager, C., Rana, S., Altmann, A., Haberkorn, U., Debus, J., Mueller, S., Huber, P. E., 2011. Investigation of tumor hypoxia using a two-enzyme system for in vitro generation of oxygen deficiency. Radiat. Oncol. 6, 35.
4. Baumann, R. P., Penketh, P. G., Seow, H. A., Shyam, K., Sartorelli, A. C., 2008. Generation of oxygen deficiency in cell culture using a two-enzyme system to evaluate agents targeting hypoxic tumor cells. Radiat. Res. 170, 651-660.
5. Blatchley, M., Park, K. M., Gerecht, S., 2015. Designer hydrogels for precision control of oxygen tension and mechanical properties. J. Mater. Chem. B: Mater. Biol. Med. 3, 7939-7949.
6. Broxmeyer, H. E., O'Leary, H. A., Huang, X., Mantel, C., 2015. The importance of hypoxia and extra physiologic oxygen shock/stress for collection and processing of stem and progenitor cells to understand true physiology/pathology of these cells ex vivo. Curr. Opin. Hematol. 22, 273-278.
7. Choi, D., Lee, W., Park, J., Koh, W., 2008. Preparation of poly(ethylene glycol) hydrogels with different network structures for the application of enzyme immobilization. Bio-Med. Mater. Eng. 18, 345-356.
8. De Miguel, M. P., Alcaina, Y., de la Maza, D. S., Lopez-Iglesias, P., 2015. Cell metabolism under microenvironmental low oxygen tension levels in stemness, proliferation and pluripotency. Curr. Mol. Med. 15, 343-359.
9. Fairbanks, B. D., Schwartz, M. P., Bowman, C. N., Anseth, K. S., 2009. Photoinitiated polymerization of PEG-diacrylate with lithium phenyl-2,4,6-trimethylbenzoylphosphinate: polymerization rate and cytocompatibility. Biomaterials30, 6702-6707.
10. Fruehauf, J. P., Meyskens Jr., F. L., 2007. Reactive oxygen species: a breath of life or death? Clin. Cancer Res. 13, 789-794.
11. Giaccia, A., Siim, B. G., Johnson, R. S., 2003. HIF-1 as a target for drug development. Nat. Rev. Drug Discov. 2, 803-811.
12. Gibson, Q. H., Swoboda, B. E., Massey, V., 1964. Kinetics and mechanism of action of glucose oxidase. J. Biol. Chem. 239, 3927-3934.
13. Han, Y. H., Xia, L., Song, L. P., Zheng, Y., Chen, W. L., Zhang, L., Huang, Y., Chen, G. Q., Wang, L. S., 2006. Comparative proteomic analysis of hypoxia-treated and untreated human leukemic U937 cells. Proteomics 6, 3262-3274.
14. Hao, Y., Lin, C. C., 2014. Degradable thiol-acrylate hydrogels as tunable matrices for three-dimensional hepatic culture. J. Biomed. Mater. Res. Part A 102, 3813-3827.
15. Hielscher, A., Gerecht, S., 2015. Hypoxia and free radicals: role in tumor progression and the use of engineering-based platforms to address these relationships. Free Radic. Biol. Med. 79, 281-291.
16. Hockel, M., Vaupel, P., 2001. Tumor hypoxia: definitions and current clinical, biologic, and molecular aspects. J. Natl. Cancer Inst. 93, 266-276.
17. Huang, Y., Zitta, K., Bein, B., Steinfath, M., Albrecht, M., 2013. An insert-based enzymatic cell culture system to rapidly and reversibly induce hypoxia: investigations of hypoxia-induced cell damage, protein expression and phosphorylation in neuronal IMR-32 cells. Dis. Models Mech. 6, 1507-1514.
18. Kirkman, H. N., Gaetani, G. F., 2007. Mammalian catalase: a venerable enzyme with new mysteries. Trends Biochem. Sci. 32, 44-50.
19. Li, C., Chaung, W., Mozayan, C., Chabra, R., Wang, P., Narayan, R. K., 2016. A new approach for on-demand generation of various oxygen tensions for in vitro hypoxia models. PLoS One 11, e0155921.
20. Liu, L., Simon, M. C., 2004. Regulation of transcription and translation by hypoxia. Cancer. Biol. Ther. 3, 492-497.
21. Millonig, G., Hegedusch, S., Becker, L., Seitz, H. K., Schuppan, D., Mueller, S., 2009. Hypoxia-inducible factor 1 alpha under rapid enzymatic hypoxia: cells sense decrements of oxygen but not hypoxia per se. Free Radic. Biol. Med. 46, 182-191.
22. Mueller, S., Millonig, G., Waite, G. N., 2009. The GOX/CAT system: a novel enzymatic method to independently control hydrogen peroxide and hypoxia in cell culture. Adv. Med. Sci. 54, 121-135.
23. Pal, P., Datta, S., Bhattacharya, P., 2000. Studies on the modeling and simulation of a sequential bienzymatic reaction system immobilized in emulsion liquid membrane. Biochem. Eng. J. 5, 89-100.

24. Park, K. M., Gerecht, S., 2014. Hypoxia-inducible hydrogels. Nat. Commun. 5, 4075.
25. Park, K. M., Blatchley, M. R., Gerecht, S., 2014. The design of dextran-based hypoxia-inducible hydrogels via in situ oxygen-consuming reaction. Macromol. Rapid Commun. 35, 1968-1975.
26. Peng, C. C., Liao, W. H., Chen, Y. H., Wu, C. Y., Tung, Y. C., 2013. A microfluidic cell culture array with various oxygen tensions. Lab Chip 13, 3239-3245.
27. Rajan, N., Narayan, A., Wu, Z., Wu, P., Ahn, C. H., Narayan, R. K., Li, C., 2013. A novel oxygen tension programmable microfluidic system (oPROMs) for in vitro cell biology studies. 2013 Transducers & Eurosensors XXVII: The 17th International Conference on Solid-State Sensors, Actuators and Microsystems (TRANSDUCERS & EUROSENSORS XXVII), 412-415.
28. Semenza, G. L., 2000. HIF-1: mediator of physiological and pathophysiological responses to hypoxia. J. Appl. Physiol. 88, 1474-1480.
29. Simon, M. C., Keith, B., 2008. The role of oxygen availability in embryonic development and stem cell function. Nat. Rev. Mol. Cell Biol. 9, 285-296.
30. Sobotta, M. C., Barata, A. G., Schmidt, U., Mueller, S., Millonig, G., Dick, T. P., 2013. Exposing cells to H2O2: a quantitative comparison between continuous low-dose and one-time high-dose treatments. Free Radic. Biol. Med. 60, 325-335.
31. Trachootham, D., Alexandre, J., Huang, P., 2009. Targeting cancer cells by ROS-mediated mechanisms: a radical therapeutic approach? Nat. Rev. Drug Discov. 8, 579-591.
32. Tse, P. H., Gough, D. A., 1987. Time-dependent inactivation of immobilized glucose oxidase and catalase. Biotechnol. Bioeng. 29, 705-713.
33. Wu, Q., Wang, L., Yu, H., Wang, J., Chen, Z., 2011. Organization of glucose-responsive systems and their properties. Chem. Rev. 111, 7855-7875.
34. Zitta, K., Meybohm, P., Bein, B., Huang, Y., Heinrich, C., Scholz, J., Steinfath, M., Albrecht, M., 2012. Salicylic acid induces apoptosis in colon carcinoma cells grown in-vitro: influence of oxygen and salicylic acid concentration. Exp. Cell Res. 318, 828-834.

We claim:

1. A photopolymerized and freeze-dried composition, comprising:
    a hydrogel formed from a polymer building block selected from the group consisting of: polyethylene glycol; (polyethylene-glycol)-diacrylate; polyvinyl alcohol; polyglycerol; collagen; gelatin; chitosan; heparin; fibrinogen; hyaluronic acid; chondroitin sulfate; pullulan; xylan; dextran; alginate; silk fibroin; or derivatives of these polymers;
    an acrylated oxygen consuming enzyme selected from the group consisting of: glucose oxidase; bilirubin oxidase tyrosinase; laccase; lysyl oxidase; monoamine oxidase; xanthine oxidase; NADPH; or cytochrome P450 oxidase, wherein the acrylated oxygen consuming enzyme is crosslinked to the hydrogel through covalent bonds and retains at least some of its catalytic activity; and
    D-trehalose; wherein the acrylated oxygen consuming enzyme is immobilized in the hydrogel, and wherein the composition produces an oxygen gradient in a solution in contact with the composition.

2. The composition of claim 1 wherein the at least one enzyme includes acrylated glucose oxidase and where in a least a portion of the acrylated glucose oxidase is crosslinked to the hydrogel through covalent bonds.

3. The composition of claim 1, wherein the at least one polymer building block is polyethylene glycol.

4. The composition according to claim 1, wherein the hydrogel and the at least one enzyme immobilized in the hydrogel are lypophilized.

5. The composition according to claim 1, wherein the acrylated glucose oxidase is present in the range of about 1 mg/mL to about 50 mg/mL.

6. The composition according to claim 1, wherein the trehalose is present in the range of about 1 mg/mL to about 50 mg/mL.

7. A photopolymerized and freeze-dried composition in contact with a solution, comprising:
    a hydrogel formed from a polymer building block selected from the group consisting of: polyethylene glycol; (polyethylene-glycol)-diacrylate; polyvinyl alcohol; polyglycerol; collagen; gelatin; chitosan; heparin; fibrinogen; hyaluronic acid; chondroitin sulfate; pullulan; xylan; dextran; alginate; silk fibroin; or derivatives of these polymers;
    an acrylated oxygen consuming enzyme selected from the group consisting of: glucose oxidase; bilirubin oxidase tyrosinase; laccase; lysyl oxidase; monoamine oxidase; xanthine oxidase; NADPH; or cytochrome P450 oxidase, wherein the acrylated oxygen consuming enzyme is crosslinked to the hydrogel through covalent bonds and retains at least some of its catalytic activity, wherein the acrylated oxygen consuming enzyme is immobilized in the hydrogel; and
    D-trehalose;
    wherein the solution in contact with the composition comprises glutathione ranging from about 2 mM to about 10 mM.

8. The composition according to claim 1, further including glucose or other enzyme substrate is present in the range of 1 about mM to about 25 mM.

9. The composition according to claim 1, wherein the concentration of crosslinked polymer falls in the range of about 5% to about 30%.

10. The composition of claim 1, wherein the composition produces an oxygen concentration gradient from solution in contact with the composition outward to surrounding solution.

* * * * *